(12) United States Patent
Shalev

(10) Patent No.: US 7,749,193 B2
(45) Date of Patent: Jul. 6, 2010

(54) VASCULAR COUPLING DEVICE

(75) Inventor: Ilan Shalev, Givataim (IL)

(73) Assignee: Activein Ltd., Kiryat-Gat (IL)

( * ) Notice: Subject to any disclaimer, the term of this patent is extended or adjusted under 35 U.S.C. 154(b) by 0 days.

(21) Appl. No.: 10/509,348

(22) PCT Filed: Mar. 26, 2003

(86) PCT No.: PCT/IL03/00254

§ 371 (c)(1),
(2), (4) Date: Mar. 24, 2005

(87) PCT Pub. No.: WO03/080166

PCT Pub. Date: Oct. 2, 2003

(65) Prior Publication Data

US 2005/0177105 A1    Aug. 11, 2005

Related U.S. Application Data

(60) Provisional application No. 60/367,263, filed on Mar. 26, 2002.

(51) Int. Cl.
*A61M 5/00* (2006.01)

(52) U.S. Cl. .............. 604/117; 604/104; 604/266; 604/513; 604/539

(58) Field of Classification Search .............. 604/96.01, 604/101.01, 102.01, 103.01, 103.07, 103.11, 604/104, 105, 265, 266, 117, 513, 539; 606/191, 606/192, 194, 198, 200
See application file for complete search history.

(56) References Cited

U.S. PATENT DOCUMENTS

| 958,854 | A | | 5/1910 | Bunn |
|---|---|---|---|---|
| 4,564,014 | A | | 1/1986 | Fogarty et al. |
| 4,808,158 | A | | 2/1989 | Kreuzer et al. |
| 5,041,097 | A | | 8/1991 | Johnson |
| 5,330,435 | A | | 7/1994 | Vaillancourt |
| 5,380,305 | A | | 1/1995 | Ghouri |
| 5,407,807 | A | | 4/1995 | Markus |
| 5,609,574 | A | * | 3/1997 | Kaplan et al. ............ 604/508 |
| 5,628,733 | A | | 5/1997 | Zinreich et al. |
| 5,638,812 | A | * | 6/1997 | Turner .................. 128/207.14 |
| 5,683,640 | A | * | 11/1997 | Miller et al. .............. 264/255 |
| 5,707,359 | A | | 1/1998 | Bufalini |
| 5,769,816 | A | | 6/1998 | Barbut et al. |
| 5,857,998 | A | * | 1/1999 | Barry .................. 604/103.03 |
| 5,885,258 | A | | 3/1999 | Sachdeva et al. |
| 5,904,670 | A | | 5/1999 | Schreiner |
| 6,077,248 | A | | 6/2000 | Zumschlinge |
| 6,146,396 | A | | 11/2000 | Kónya et al. |
| 6,183,450 | B1 | | 2/2001 | Lois |
| 6,547,760 | B1 | * | 4/2003 | Samson et al. ......... 604/103.01 |
| 6,955,661 | B1 | * | 10/2005 | Herweck et al. ............ 604/264 |
| 6,958,059 | B2 | * | 10/2005 | Zadno-Azizi .............. 604/509 |
| 2002/0128543 | A1 | | 9/2002 | Leonhardt |
| 2003/0167038 | A1 | * | 9/2003 | Yozu et al. ............. 604/101.01 |

FOREIGN PATENT DOCUMENTS

| EP | 1490137 | 12/2004 |
|---|---|---|
| FR | 2 808 991 | 11/2001 |

\* cited by examiner

*Primary Examiner*—Kevin C Sirmons
*Assistant Examiner*—Bhisma Mehta

(57) ABSTRACT

A venous port for withdrawal of fluid in which one or more extensions are provided which can selectively extend to remove impediments from an aperture of the port.

51 Claims, 6 Drawing Sheets

VASCULAR COUPLING DEVICE

RELATED APPLICATIONS

The present application is a U.S. national application of PCT Application No. PCT/IL03/00254, filed on Mar. 26, 2003. This application also claims the benefit under 35 U.S.C. §119(e) of U.S. Provisional Application No. 60/367,263. All the disclosures of the above listed applications axe incorporated herein by reference.

FIELD OF THE INVENTION

The present invention relates to fluid withdrawal or delivery from a body cavity.

BACKGROUND OF THE INVENTION

Connection of a catheter to a blood vessel, for example a vein, is an important medical procedure that allows withdrawal of fluid, for example blood samples, or delivery of fluid, for example nutrients, for a few days up to a few weeks. In the process of fluid delivery and/or withdrawal, for example, the catheter is periodically pulled out of one vein area and inserted into another vein area, for example, every five days.

FIGS. 1A through 1F illustrate typical prior art catheters and a variety of problems that typically occur, resulting in obstruction of fluid withdrawal, for example, from a vein 130.

FIG. 1A illustrates a catheter 118, typically comprising a hollow tube, a portion of which is typically implanted vein 130 by piercing a section of skin 102 and wall of vein 130. By so doing, a catheter front inlet 134 lies within vein 130.

Vein 130 is most desirable when it is located just below skin 102 so that the outline of vein 130 can be seen through skin 102. This allows a relatively painless and fast percutaneous maneuver to poke catheter 118 into vein 130. In FIG. 1F, prior art catheter 118 is shown installed percutaneously in an arm 104 into vein 130 whose outline is seen through skin 102. For the purpose of delivery of nutrients to vein 130, catheter 118, for example, is attached to a flexible sac 106 containing a fluid 108. Sac 106 is, for example, held by a hook 112 that is connected to a stand 110. Fluid 108 is distributed, for example, by gravity action through catheter 118 to vein 130. Additionally or alternatively, fluid 108 is distributed with pressure, for example by a perfusion system that increases the rate of fluid movement for the purpose of decreasing the introduction span of fluid 108.

In prior art catheters, FIGS. 1A-1F, fluids are typically transported from vein 130 through catheter front inlet 134. For example, multiple fluid samples are withdrawn from the patient through catheter front inlet 134 in vein 130. During fluid withdrawal for a moderate period of time, leaving catheter 118 in one place, such as vein 130, for as long as possible, for example several weeks, is advantageous.

Unfortunately, when catheter 118 is left in one place for a few days or even as briefly as one day, particularly when fluid withdrawal is not on a continuous basis, blockage of catheter front inlet 134 often occurs. While blockage may occur either during fluid introduction or withdrawal from a patient, it often occurs in a shorter span of time during fluid withdrawal as blockages are pulled toward front inlet 134. During fluid introduction, for example, blockages tend to be displaced and/or removed away from catheter inlet 134 by the pressure of the movement of fluid out of catheter 118 into vein 130. FIGS. 1A-1E illustrate the various blockages that occur, often more readily, during fluid withdrawal from vein 130.

FIG. 1B illustrates one form of blockage when the surrounding cavity walls 150 collapse, blocking catheter front inlet 134. FIG. 1C demonstrates another form of blockage where a clot 160, consisting of solid particles from body fluid, forms and blocks catheter front inlet 134. Clot 160, for example, may form either beyond front catheter inlet 134, as shown, or within catheter 118, in either case preventing fluid withdrawal. In some cases, clot 160 forms as a plug both inside and outside of inlet 134. FIG. 1D demonstrates another form of blockage where a section of inflamed tissue 170 blocks front inlet 134. FIG. 1E illustrates still another form of blockage that occurs when vein valves 194, a regularly occurring part of the body's vein system, block inlet 134.

In all of these cases, vein 130 becomes unsuitable, often permanently, for further fluid withdrawal. When vein 130 becomes unsuitable, catheter 118 must be taken out of vein 130 and inserted into another vein 130. Unfortunately, besides the discomfort associated with reinsertion of catheter 118 into vein 130, there is a limit to the number of fluid exchange areas, such as vein 130, that, for example, may be percutaneously accessed with catheter 118.

When easily accessed venous fluid withdrawal areas are exhausted, less optimal areas must be utilized, such as, for example, veins that are somewhat tortuous, often requiring more than one attempt for a successful introduction of catheter 118 into vein 130. Eventually, when percutaneously accessible fluid exchange areas are exhausted, fluid withdrawal and/or introduction, for example, can take place only through alternative means such as a surgically placed shunt. The placement of a shunt is a relatively expensive and hazardous procedure in comparison to percutaneous access of vein 130 with catheter 118.

Zumschlinge, U.S. Pat. No. 6,077,248 teaches a catheter that is used for fluid withdrawal from body cavities with a needle that retracts into a flexible housing to prevent the needle from causing tissue damage due to tissue movement against the needle.

SUMMARY OF THE INVENTION

An aspect of an embodiment of the present invention provides a catheter with an opening at its tip for the purpose of fluid withdrawal from a vein, with one or more extendible extensions that aid in this process of fluid withdrawal. Said extensions maintain at least two positions in relation to said catheter, one position being near said catheter and a second position in which at least part of the extension is away from said catheter. When these one or more extensions are positioned away from the catheter, they aid in fluid withdrawal from a vein, for example, in one or more of the following manners:

a) removing and/or displacing tissue or a blockage from a catheter;

b) transposing a catheter inlet away from tissue or a blockage;

c) aiding in the break-up and/or evacuation of blocking material such as a clot that forms outside the catheter;

d) opening one or more coverings that prevent clots from forming inside the catheter;

e) distancing venous valves from a catheter inlet so they do not block fluid withdrawal.

In an exemplary embodiment of the invention, the catheter is implanted to withdraw fluids from a vein. In such an embodiment, the catheter functions as a venous port which is adapted to be implanted in a surface vein.

In an exemplary embodiment of the invention, the extensions displace impediments that are forward of the catheter. Alternatively or additionally, the extensions displace the sides of the vessel.

In an embodiment of the invention, one or more balloon extensions fill with fluid and expand, thereby moving away from the catheter. In another embodiment of the invention, one or more deformable extensions deform at a deformation area and extend away from said catheter. In another embodiment of the invention, one or more resilient extensions are contained within a sheath and, upon being released from the sheath, extend away from the catheter.

In an embodiment of the present invention, extension of the extensions is operated manually, for example by squeezing a fluid bulb that forces fluid into the extensions, or by advancing, twisting or retracting an element that activates the extensions by mechanical coupling. Alternatively, extension of the extensions is operated by an automatic mechanism that is powered, for example, by a motor.

In various embodiments of the present invention, extension of the extensions takes place prior to, during and/or following fluid withdrawal. Additionally or alternatively, extension of the extensions takes place irrespective of fluid withdrawal from a vein, for example, periodically.

In an embodiment of the invention, a catheter with one or more extendible extensions has one or more side openings in its walls for fluid withdrawal in addition to or instead of a catheter front inlet. When said extensions are near the catheter, the one or more side openings in the walls are optionally covered, thereby preventing body fluid from entering the catheter and forming a clot. When the extensions extend away from the catheter, fluid withdrawal is allowed through the side openings. Said side openings optionally allow fluid withdrawal even when the opening at the catheter tip is blocked.

In an embodiment of the invention, a part of the extensions cover said openings. Additionally or alternatively, the side openings are covered by body tissue that may be displaced from the side openings by the extension of the extensions.

In some embodiments of the invention, the catheter is adapted for removing and/or displacing blockages during introduction of fluid into a vein, even if a continuous "drip" is not provided. Additionally or alternatively, a catheter is provided with one or more extendible extensions that extend to aid in removing and/or displacing blockages during withdrawal and/or introduction of fluid from other blood vessels, for example an artery. Additionally or alternatively, a catheter is provided with one of more extendible extensions that extend to aid in removing and/or displacing blockages during withdrawal and/or introduction of fluid from body cavity, for example, a pleural sac.

Optionally, the catheter or the extensions elute one or more materials that prevent clots, infection and/or inflammation, for example, anti-clotting factors, antibiotics or steroids. For example, the catheter may be coated with an eluting matrix or be formed with filled micropores. Alternatively or additionally, such materials may be provided, for example, via drip, through a port in the catheter.

It should be noted that while the term "catheter" is used, any type of port may be used, including a short port adapted for entering a vein, to which a fluid conveying tube is attached outside of the body. Such a port may be, for example, shorter than, for example, 10 or 5 cm, and may have a section outside the body which is shorter than, for example, 10 or 5 or 1 cm. This external section may be, for example, thicker or winged, as shown in FIG. 2E, to prevent entry into the body and/or may include an inner threading for attachment of a tube. In some cases, such a port includes a seal, for example, a solid seal that is pierced by a needle section of said tube. Another exemplary type of seal is a flap valve, for example formed by two abutting flaps of soft material, which may be deformed by pushing a tube through them and/or by external pressure (e.g., by pressing on either side with a finger). Other valves, for example in a lumen of the catheter may be used instead or as well.

In some embodiments of the invention, the port or catheter is sharpened at its tip for introduction. In others, a separate introducer sheath may be used.

There is thus provided in accordance with an exemplary embodiment of the invention, apparatus adapted to be placed through a body tissue and implanted in a vein for the purpose of intake of fluid through an aperture thereof, comprising:

a hollow tube defining at least one aperture; and at least one extension operative to be at at least two positions with respect to said aperture, a first position near said aperture and a second position in which at least part of said extension extends away from said aperture, wherein extension of said at least one extension from said first position to said second position in relation to said aperture is operative to displace at least one fluid intake impediment from said aperture.

In an exemplary embodiment of the invention, there is provided a venous port adapted to be placed through a body tissue and implanted in a surface vein for the purpose of unimpeded intake of fluid through an aperture thereof, comprising:

a hollow tube defining at least one aperture configured for the unimpeded intake of fluid when implanted in the surface vein; and a plurality of extensions, each operative to be at at least two positions with respect to said at least one aperture, a first position near said at least one aperture and a second position in which at least part of each of said plurality of extensions extends away from said at least one aperture, wherein if said at least one aperture is blocked by an impediment, relative movement of said plurality of extensions with respect to said at least one aperture, from said first position to said second position, operates to dislodge the impediment from said at least one aperture and to open at least one blood passageway among said plurality of extensions;

wherein said hollow tube has a portion sized and shaped to prevent the insertion of more than 10 cm of said hollow tube in the body of a patient when implanted so that said hollow tube is adapted to be implanted in the surface vein and withstand the unimpeded intake of fluid for a period of one or more days.

Optionally, said aperture comprises a front opening at a front end of said tube. Alternatively or additionally, said aperture comprises one or more side openings in a side of said tube.

In an exemplary embodiment of the invention, said aperture comprises at least one front opening at a front end of said tube and at least one side opening in a side of said tube.

In an exemplary embodiment of the invention, said impediment comprises an aggregate of solid material.

In an exemplary embodiment of the invention, said impediment is down-flow from said hollow tube.

In an exemplary embodiment of the invention, said impediment is at least partly within said hollow tube.

In an exemplary embodiment of the invention, wherein said impediment comprises a venous valve.

In an exemplary embodiment of the invention, said impediment comprises body tissue. Optionally, said body tissue is inflamed.

In an exemplary embodiment of the invention, said hollow tube is adapted to be implanted in a vein for the purpose of unimpeded intake of fluid for a period of one or more weeks.

In an exemplary embodiment of the invention, said hollow tube is adapted to be implanted in a vein for the purpose of unimpeded intake of fluid for a period of one or more months.

In an exemplary embodiment of the invention, the apparatus comprises an activating mechanism. Optionally, said activating mechanism causes said extensions to extend from said first position to said second position. Alternatively or additionally, said activating mechanism causes said extensions to un-extend from said second position to said first position. Alternatively or additionally, said activating mechanism comprises a locking mechanism that, when unlocked, allows said extensions to extend from said first position to said second position. Alternatively or additionally, at least a portion of said activating mechanism is external to said body tissue. Alternatively or additionally, a portion of said one or more extensions is external to said body tissue. Alternatively or additionally, the activating mechanism is manually activated.

In an exemplary embodiment of the invention, the activating mechanism is automatically activated.

In an exemplary embodiment of the invention, said extension of said extensions occurs prior to said fluid withdrawal. Alternatively or additionally, said extension of said extensions occurs during said fluid withdrawal. Alternatively or additionally, said extension of said extensions occurs following said fluid withdrawal. Alternatively or additionally, at least some extension of said extensions takes place irrespective of fluid exchange. Alternatively or additionally, at least part of said one or more extensions, overlaps a front end of said tube when said extensions are in a first position. Alternatively or additionally, said at least one aperture is covered by said one or more extensions in said first position. Alternatively or additionally, said apertures are arranged to be covered in said first position. Alternatively or additionally, one or more of said catheter and said extensions comprise a material that prevents or retards aggregation of solids from said body fluid. Alternatively or additionally, one or more of said catheter and said extensions comprise a material that prevents or retards clot formation. Alternatively or additionally, one or more of said catheter and said extensions comprise a material that prevents or retards body tissue inflammatory response. Alternatively or additionally, one or more of said catheter and said extensions comprise a material that prevents or retards bacteria colonization. Alternatively or additionally, the one or more extensions comprise expendable elements. Optionally, said one or more balloons expand when filled with expansion fluid. Optionally, said apparatus comprises an activating mechanism including a reservoir containing expansion fluid connected to said one or more balloon extensions.

In an exemplary embodiment of the invention, said expansion fluid comprises a material that affects the formation of impediments and wherein said balloon is at least partly permeable to said material.

In an exemplary embodiment of the invention, the one or more extensions are moved, in relation to the aperture, from the first position to the second position, so as to open one or more blood passageway among the plurality of extensions.

In an exemplary embodiment of the invention, the one or more extensions comprise an extension with a deformable area. Optionally, when said deformable area deforms, said extension extends from said first position to said second position. Alternatively or additionally, when said extension un-extends from said second position to said first position, said deformable area returns to its pre-deformed state.

In an exemplary embodiment of the invention, the one or more extensions comprise resilient extensions.

In an exemplary embodiment of the invention, the apparatus comprises a sheath for selectively controlling an extension position of said extensions. Optionally, when said at least one extension exits distally from said sheath they deflect radially.

In an exemplary embodiment of the invention, the apparatus comprises an extension tube of which said extensions form a distal section, wherein axial distal motion of said extension tube causes said extensions to extend.

In an exemplary embodiment of the invention, a distal section of said extension tube is axially fixed to a front of said hollow tube and wherein said extension tube is slotted.

In an exemplary embodiment of the invention, said extensions are adapted for an arm vein.

In an exemplary embodiment of the invention, said extensions are adapted for a non-vein vessel.

In an exemplary embodiment of the invention, said positions are axially displaced. Alternatively or additionally, said positions are radially displaced.

BRIEF DESCRIPTION OF THE DRAWINGS

Exemplary non-limiting embodiments of the invention will be described with reference to the following description of embodiments in conjunction with the figures. Identical structures, elements or parts which appear in more than one figure are generally labeled with a same or similar number in all the figures in which they appear, in which.

DETAILED DESCRIPTION OF EXEMPLARY EMBODIMENTS

Figure 2A:
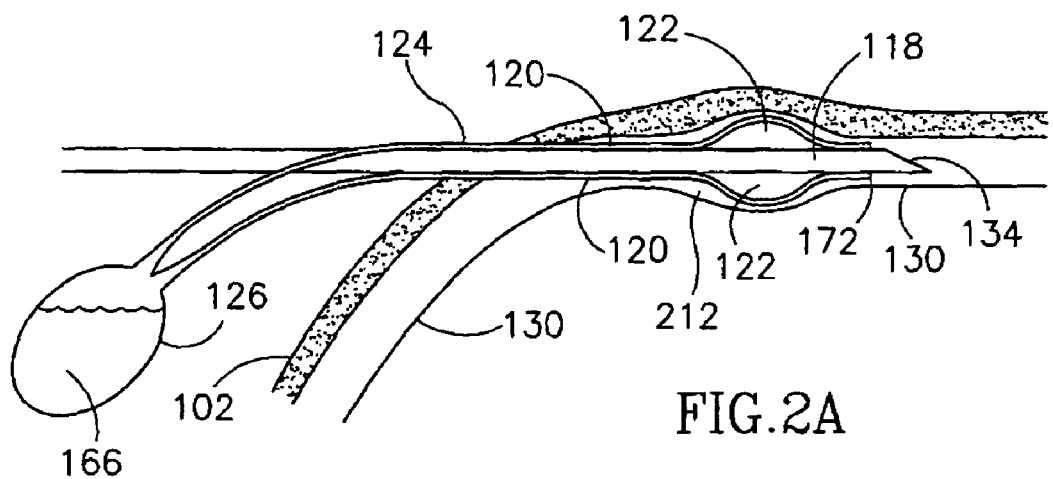
FIG. 2A is a cut-away side view of a catheter with multiple balloon extensions within a vein, according to an exemplary embodiment of the present invention.

In an exemplary embodiment of the invention, a portion of catheter 118 is provided with one or more extendible extensions, in one or more configurations, that aid in fluid withdrawal from vein 130. FIG. 2A is a cut-away side view of balloon extensions 122 extending away from catheter 118. Balloon extensions 122 extend away from catheter 118 when they are caused to expand by the introduction of an expansion fluid 166, such as sterile water, saline, oxygen or nitrogen, introduced through expansion inlet 124 and via one or more passageways 120 into one or more suitable chambers. Extension of balloon extension 122 away from catheter 118 aids in preventing, or prevents, blockage of catheter 118, for example, by one or more of:

a) removing and/or displacing tissue or a blockage from a catheter;

b) transposing a catheter inlet away from tissue or a blockage;

c) aiding in the break-up and/or evacuation of blocking material such as a clot that forms outside the catheter;

d) opening one or more coverings that prevent clots from forming inside the catheter;

e) distancing venous valves from a catheter inlet so they do not block fluid withdrawal.

Expansion inlet 124 through which expansion fluid is introduced into balloon extension 122, is, for example, attached to a reservoir 126, located outside surface 102, containing expansion fluid 166. Squeezing flexible reservoir 126 forces expansion fluid 166 into balloon extensions 122, causing their extension. Additionally or alternatively, reservoir 126 has rigid walls and a pump mechanism, similar to the design of a syringe. In this embodiment, expansion fluid 166 is pumped from reservoir 126 as one would express fluid from a syringe. Once expansion fluid 166 has caused extension of balloon extensions 122, release of pressure on reservoir 126 allows the pressure of a balloon extension skin 212 to push fluid out of balloon extensions 122, back into reservoir 126.

In an embodiment of the present invention when balloon extensions 122 expand to a position where they are extending away from said catheter 118, catheter front inlet 134 extends beyond a front edge of balloon extensions 172. Movement of catheter front inlet 134 aids in physically pushing against a blockage removing and/or displacing a blockage, thereby helping to open a passageway. Alternatively, when balloon extensions 122 expand, front edge 172 expands to a position beyond catheter front inlet 134. In this embodiment, blockages that have adhered to catheter front inlet 134 and front edge 172, lose their adhesion to catheter front inlet 134 due to this movement. With expansion of balloon extensions 122, the blockage further loses its adhesion to front edge 172 so the blockage moves and/or is displaced with the flow of fluid, allowing fluid exchange.

In an embodiment of the invention, different catheters 118 and balloon extensions 122 are placed in veins 130 for different lengths of time, for example, up to a week, up to a month and over a month. Each of these time periods can create different problems, which may make different catheter 118 designs desirable to ensure smooth fluid withdrawal from vein 130.

Examples of reasons for differences in implantation time for which different designs of catheter 118 may be desirable, include, for example: a) damage to vein 130 and surrounding tissue, b) tissue inflammation, c) fluid coagulation and/or, d) local infection in vein 130.

Figure 1A:
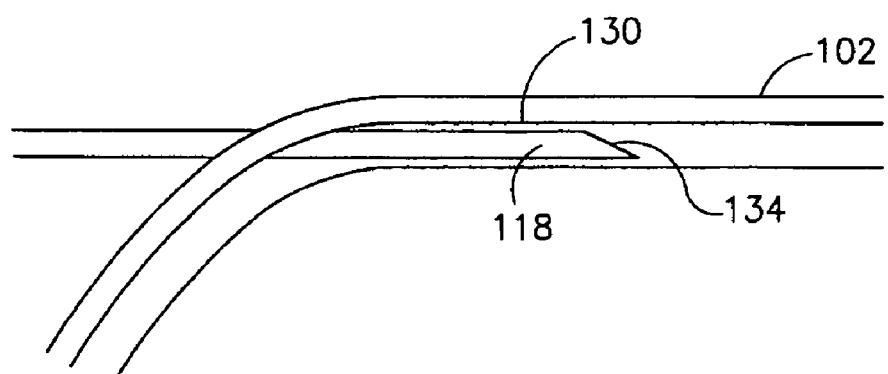
FIG. 1A is a schematic side view of a catheter in a healthy vein, according to a prior art embodiment.
Figure 1B:
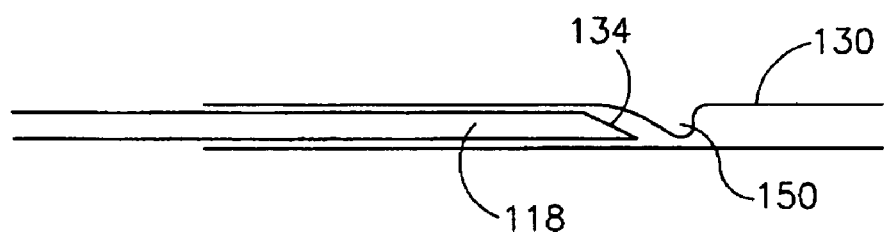
FIG. 1B is a schematic side view of a catheter in a partially collapsed vein, according to a prior art embodiment.
Figure 1C:
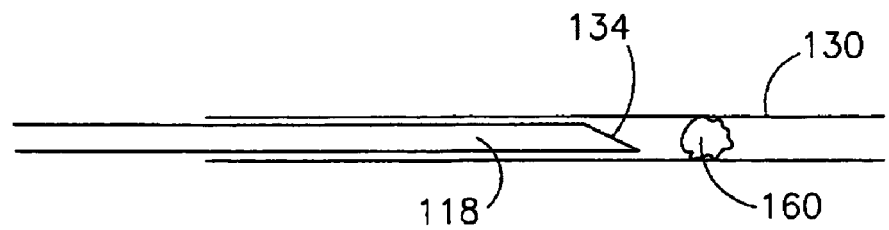
FIG. 1C is a schematic side view of a catheter in an obstructed vein, according to a prior art embodiment.
Figure 1D:
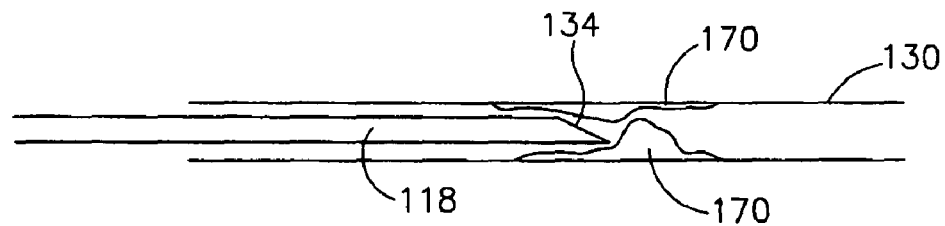
FIG. 1D is a schematic side view of a catheter in an inflamed vein, according to a prior art embodiment.
Figure 1E:
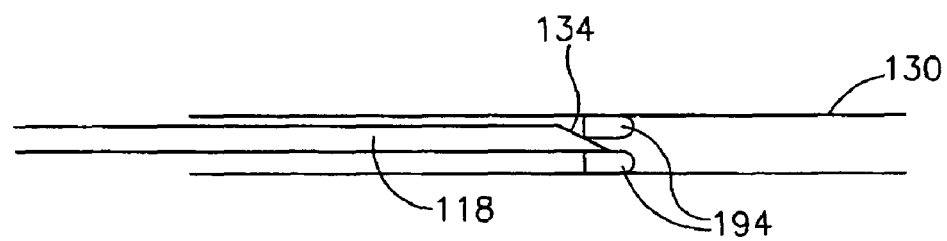
FIG. 1E is a schematic side view of a catheter in a vein, according to a prior art embodiment.

Some tissue portions may be sucked into catheter front inlet 134 during fluid withdrawal, as shown in FIG. 1E for flaps, during the first week of implantation. Between one week and one month, catheter 118 may poke into vein wall 130, weakening it greatly and may actually pierce through vein wall 130 causing sporadic blood leakage into surrounding tissue.

An operator may pull back on catheter 118 during fluid withdrawal to center catheter inlet 134 in vein 130 during fluid withdrawal.

For periods of implantation greater than a month, the hole in vein wall 130 may enlarge to the point of remaining open continually, with blood leakage from vein 130 dispersing in the tissue surrounding vein 130. With significant leakage of blood into tissue surrounding vein 130, patient anemia and weakness can result.

In addition to physically piercing vein wall 130, inflammation, the body's reaction to a foreign body, may begin to occur during the first week of implantation of catheter 118. Inflammation may continue so that during the first month of implantation, vein 130 may appear as in FIG. 1D with accompanying impediment of flow through catheter tip 134. Inflamed tissue 170 may continue to thicken past the first month, resulting in a buildup of tissue outside vein walls 130, impinging on surrounding blood flow and tissue function.

Fluid coagulation often occurs in the first week and may progress until there is a clot 160 as illustrated in FIG. 1C during the period of one week to one month. Following one month, clot 160 may increase in size until it becomes a bolus from which pieces break off that can cause tissue and/or organ damage around the body. Pieces that break off clot 160 may cause, for example, amaurosis fugax, periodic blockage of vision as the clot pieces pass through the eye. However, such signals are not always the case and a stroke or heart attack may result from embolism blockage caused by the traveling clot pieces.

Figure 1F:
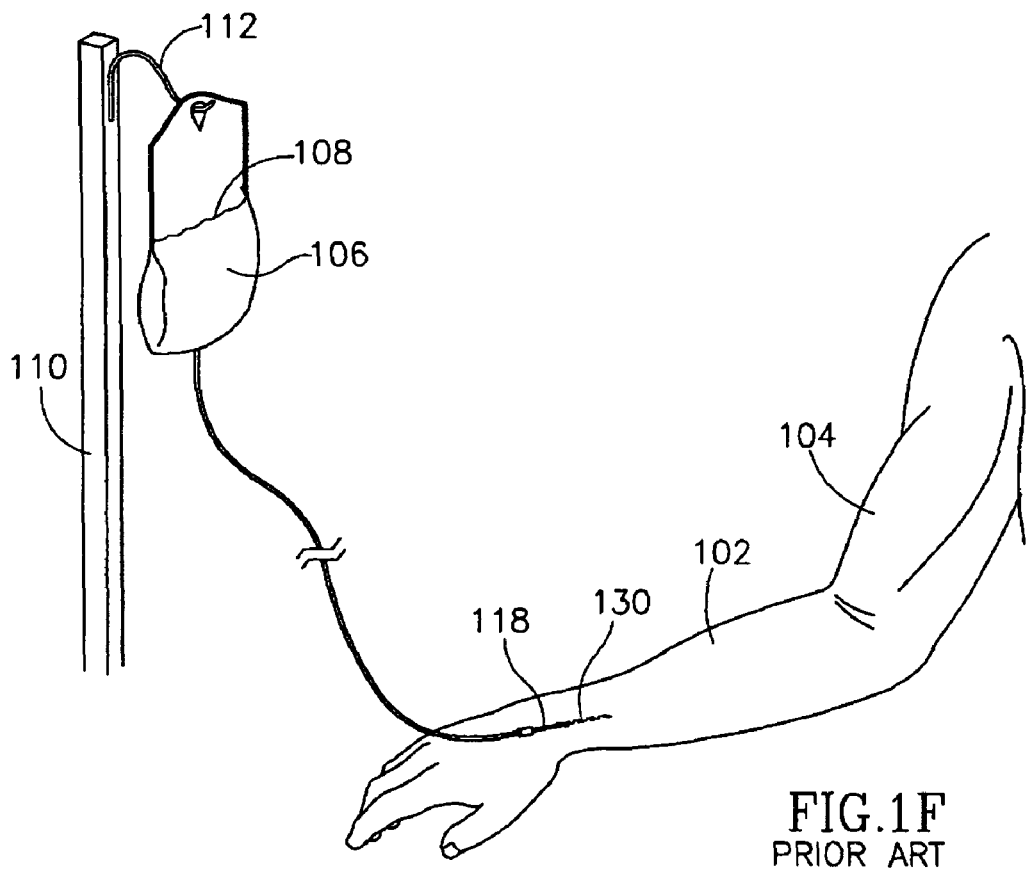
FIG. 1F is a view of a catheter installed in an arm vein, according to a prior art embodiment.

Clot 160 and/or inflammation 170 may provide a nidus for bacteria growth so that during the period of one week to one month, local infection may form in vein 130 near catheter inlet 134. A local infection in vein 130 may appear as a small red area on arm 102 in FIG. 1F, often surrounding the insertion point of catheter 118. From one week to one month, the local infection in vein 130 may present with a red streak along the length of arm 102, a sign that the infection has spread along the local lymph nodes. Beyond one month, pain and swelling in the lymph nodes, for example, may accompany the red streak, signifying infection spread to the lymph nodes and possibly beyond.

Variations in the design of catheter 118 and balloon extensions 122 may be desirable based upon the period in which catheter 118 is to be implanted in vein 130. In an exemplary embodiment of the present invention, extension of balloon extensions 122, occurs prior to, during and/or following fluid withdrawal, for example, when catheter 118 remains in vein 130 for up to a week. Further, when catheter 118 remains in vein 130 for up to a week, expansion of balloon extensions 122, for example, or other extension embodiments, may be manually controlled, for example by an operator. In a manual control, an operator, for example, squeezes reservoir 126, causing fluid to expand balloon extensions 122.

However, when catheter 118 remains in vein 130 for a month or more, vein 130 may have a tendency to react to catheter 118 forming, for example, inflammation and/or swelling along its walls that block catheter 118. When catheter 118 remains in vein 130 a month or longer, extension of balloon extensions 122 for example, may be irrespective of fluid withdrawal. For example extension of balloon extensions 122 may be periodic, for example every hour or half hour additionally or alternatively to extension of balloon extensions 122 prior to, during and/or following fluid withdrawal. When expansion of balloon extensions 122 occurs irrespective of fluid withdrawal, extension is controlled, for example, by a mechanism. In automatic control, a mechanically induced squeezing pressure from a pump mechanism, for example, forces fluid from reservoir 126, causing expansion fluid 166 to expand balloon extensions 122.

In an exemplary embodiment of the invention, automatic extension is provided by a sensor (not shown) which detects the insertion of a fluid withdrawal needle, e.g., using a pressure or magnetic sensor. Alternatively or additionally, the insertion of the needle mechanically activates a fluid reservoir or a locking mechanism (described below for a mechanical extension). Alternatively or additionally, a vacuum sensor activates the extension when it senses suction caused by an attempted withdrawal. An example of manual extension is providing a fluid reservoir at a location where a technician will apply pressure while introducing a needle for fluid withdrawal. In some embodiments, an opposite linkage is desired. When a user manually activates the extension(s), a fluid collection mechanism is automatically activated (e.g., a vacuum collection vial is opened optionally after a short delay), to collect the fluid passing through catheter 118. It should be noted that various delay and/or synchronization mechanisms can be provided using mechanical or electronic means. Electronic or computer circuitry may be used for periodic activation, described herein, as well.

Optionally, one or more drugs or other materials may be eluted or otherwise released by catheter 118 and/or balloon extensions 122. In an exemplary embodiment fluid within balloon extensions 122 with semipermeable balloon extension skin 212 contain a drug or drugs that prevent and/or inhibit aggregation of solids from body fluid. In catheters 118 that are implanted for a short term, for example one week or less, optionally a short-acting anti-aggregate may be utilized. In catheters that are implanted for a longer term, for example more than a week and less than a month, a longer acting anti-aggregate may be utilized. In catheters that are implanted for longer than a month, additional anti-aggregates may be used, for example warfarin sodium, that affects the coagulatory tendency of blood solids may be included.

In an exemplary embodiment fluid within balloon extensions 122 with semipermeable balloon extension skin 212 contain a drug or drugs, for example a steroid, that prevent and/or inhibit body inflammatory response to catheter 118 and/or its extensions. In catheters 118 that are implanted for a short term, for example one week or less, a short-acting anti-inflammatory agent may be utilized. In catheters that are implanted for a longer term, for example more than a week and less than a month, a longer-acting anti-inflammatory agent may be used. In catheters that are implanted for longer than a month, a long-acting anti-inflammatory agent for example that is not water soluble, may be used.

In an exemplary embodiment fluid within balloon extensions 122 with semipermeable balloon extension skin 212 contain a drug or drugs, for example an antibiotic, that prevent and/or inhibit bacteria from colonizing tissue surrounding catheter 118. In catheters 118 that are implanted for a short term, for example one week or less, a narrow spectrum antibiotic may be utilized. In catheters that are implanted for a longer term, for example more than a week and less than a month, a wider spectrum antibiotic may be used. In catheters that are implanted for longer than a month, a wide spectrum antibiotic may be used, for example a new generation, single dose per 24 hour antibiotics.

Optionally, drug or drugs that prevent and/or inhibit aggregation of solids from body fluid, inflammation of body tissue and/or colonization of bacteria fluid may be introduced through catheter 118.

An optional difference in structure of catheter 118 and balloon extensions 122 (or other types of extension, described below), based upon length of implantation in vein 130, may be the attachment and flexibility between these two components. Balloon extensions 122 may be individually attached, for example with an adhesive, to catheter 118. Adhesive, for example, may provide a less robust attachment between balloon extensions 122 and catheter 118. For example, when catheter 118 is used for a week in vein 130 and/or in an area of lower stress such as along a straight area of an extremity, attachment between balloon extensions 122 and catheter 118 may be with an adhesive.

Balloon extensions 122, for example, may be designed so they are attached to a collar that, for example, surrounds and/or is attached to catheter 118. When catheter 118 is used in a vein 130 for a period of a month or more, attachment of balloon extensions 122 to catheter 118, for example, may be with a collar that surrounds catheter 118. Additionally or alternatively, when catheter 118 is used in an area of higher stress such as near a joint, for example the wrist, where there is a more movement, attachment of balloon extension 122 to catheter 118 may be with a collar.

Alternatively, catheter 118, comprises a flexible material, for example a silicone rubber, and/or rigid material, for example a metal or an epoxy. Optionally, a determining factor of catheter 118 material, for example, may be the length of time that catheter 118 is placed in vein 130. During placement in vein 130 of periods less than a week, for example, catheter 118 and its extensions, may be of a rigid material as the irritation that accompanies rigid material does not have enough time to cause significant harm to surrounding tissue. However, when catheter 118 and its extension are placed in a vein 130 for periods longer than a week, for example, they may require flexible materials to prevent undue irritation to surrounding tissue.

It should be appreciated that the time scales described above are exemplary and in actual practice and/or for a particular patient, they may vary.

Figure 2B:
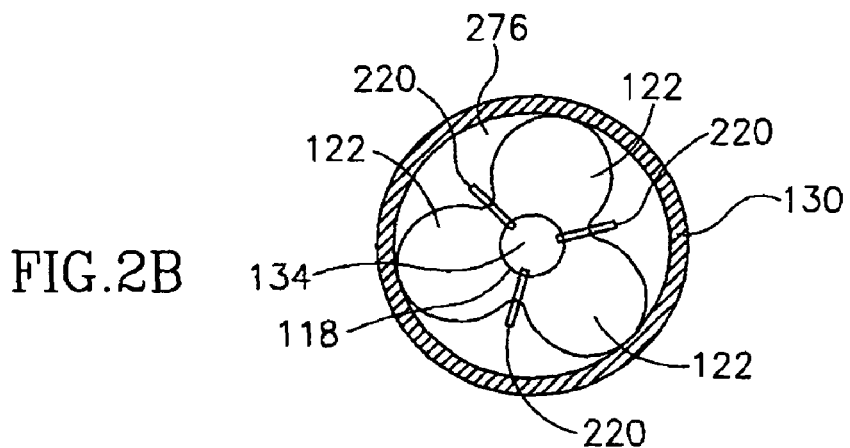
FIG. 2B is a frontal view of a catheter with multiple balloon extensions, according to an exemplary embodiment of the present invention.

FIG. 2B shows a frontal view of balloon extensions 122 of FIG. 2A within a cavity, 276 inside walls of vein 130. Expanded balloon extensions 122 push walls of vein 130 away from catheter front inlet 134. Three balloon extensions 122 allow uniform expansion around the inner diameter of walls of vein 130. While three balloon extensions 122 are shown, alternative numbers are within the scope of this invention. For example, only one or two balloon extensions 122 may be provided, so that a portion of the circumference wall of vein 130 is caused to expand to remove and/or displace blockages that prevent passive fluid exchange and or fluid exchange under pressure. A design with a single balloon extension 122, for example, may be advantageous in that it is compact and may be easily manipulated in a cavity with a small bore, such as one millimeter in diameter. Alternatively, more than three, for example, four, five or ten such balloon extensions 122 are provided, for example, for use in a vein 130 with more resilient walls, for example a hepatic vein.

In an exemplary embodiment, a portion of catheter 118 containing extension sections, such as balloon extensions 122, or other extension embodiments, is poked through skin 102 and into a body tissue, for example, vein 130. The portion of catheter 118 that is within vein 130, for example, is 2 centimeters in length. Additionally or alternatively, it could be as much as four, eight or ten centimeters or as little as a half centimeter, for example, dependent upon the tissue type and or tissue cavity diameter. The portion that is outside can be, for example, 0.5 or 1 cm with a tube connected or integrally formed therewith.

In an exemplary embodiment, catheter 118 containing extension sections, such as balloon extensions 122, or other extension embodiments, is a hollow tube of a specific diameter, for example 3 millimeters, for introduction into vein 130 along the subject arm. However, the scope of the embodiments of this invention, relates to connection of catheter 118 to any size vein 130 and therefore it is contemplated to be of an appropriate size for introduction into vein 130 of any size. Depending upon the bore of vein 130 into which it is to be introduced, catheter 118, could be 5 millimeters, a centimeter, or as much as 5 centimeters in diameter. Alternatively, catheter 118 could be 3 millimeters, 1 millimeter or even a half-millimeter in diameter dependent upon the diameter of vein 130.

In an exemplary embodiment of the present invention, catheter 118 and balloon extensions 122, and/or other extension embodiments, comprise a biocompatible material, for example a biocompatible plastic or rubber. Additionally or alternatively, catheter 118 and/or its various extension embodiments are coated with a material that thwarts and/or does not promote aggregation of solid materials from body fluid. In an exemplary embodiment, catheter 118 and/or its various extension embodiments are coated, and/or impregnated, with a steroid that prevents and/or inhibits body inflammatory response. Additionally or alternatively, catheter 118 and/or its various extension embodiments are coated, and/or impregnated, with an antibiotic that prevents bacteria from colonizing tissue surrounding catheter 118. The antiaggregate, steroid and/or antibiotic, for example, are slow-release compounds that are released, for example, over a period encompassing the period in which catheter 118 is implanted in body tissue, for example a period of several months.

Optionally, one or more of extensions 122 extend forward, for example being flexible in their distal side end, so that they approach, reach and/or axially pass port 134.

In an embodiment of the present invention, fluid withdrawal takes place through catheter front inlet 134. Additionally or alternatively, fluid withdrawal occurs through one or more side openings 220 along catheter 118. Optionally, one or more side openings 220 are covered by one or more balloon extensions 122, or other extension embodiments, as they are near catheter 118 and open when extended away from catheter 118.

Additionally or alternatively, one or more side openings 220 are covered by body tissue such as wall of vein 130 when balloon extensions 122, or other extension embodiments, are near catheter 118. Side openings 220 are open and free of body tissue such as wall of vein 130 when balloon extensions 122 extend away from catheter 118. While side openings 220 are covered, they remain free of build-up or solid deposits from body fluid. When catheter front inlet 134 becomes blocked, side openings 220 will, for example, provide alternative openings for fluid introduction and/or withdrawal.

Optionally, extensions 122 operate in a similar manner for port 134 as for side openings 220.

Vein 130, for example, has weaker walls than an artery and other body tissue, for example, as well as a unique valve system that may be prone to being damaged. Due to these features of vein 130, expansion of balloon extensions 122 may be limited to a maximum diameter to prevent damage to surrounding tissue. For use in vein 130 with a small bore, for example an arm vein, balloon extensions 122 may move outward from catheter a maximum of 1 millimeter, while in vein 130 with a larger bore, for example a hepatic vein, balloon extensions 122 may move outward from catheter a maximum of 2 millimeters.

In an embodiment of the invention, different catheters 118 and balloon extensions 122 are placed in other blood vessels and/or body tissue besides vein 130. Each of these tissues can create different problems, for which different design variations may be provided. Examples of tissue differences for which different designs of catheter 118 may be provided, include, for example, arteries, striated muscle and/or sensitive organ tissue.

For example, the multi-layered, robust nature of artery walls, may tend to impede extension of balloon extensions 122. Additionally or alternatively, in areas where collateral circulation is diminished or non-existent, balloon extensions 122 may cause impediment of blood flow that endangers the viability of surrounding tissue and/or organs.

Striated muscle may create pressure against an implanted catheter 118, causing impediment in fluid exchange and irritation and/or perforation of blood vessels. Further, severe disruption of fluid exchange with leakage into surrounding tissue may occur during movement of the muscle.

Implantation of catheter 118 in or near sensitive tissue, for example may result in damage, perhaps of an irreversible nature. For example, if balloon extensions 122 press against nerve tissue, it may result in damage to the nerve, with resultant problems in nerve conduction, sensation and/or function.

To allow implantation within an artery, for example, where the walls are multi-layered and more robust, balloon extension 122 may move away from catheter 118 a maximum of several millimeters independent of the arterial bore. Additionally or alternatively, balloon extensions 122 comprises a material with greater resilience, resulting in greater extension force. In an artery, for example a coronary artery, with a small bore, balloon extensions 122 may simply be limited in the distance away from catheter 118 that they can expand away from catheter 118 by the configuration of the surrounding tissue.

Similarly, in a sac containing pus within a body tissue, for example a striated muscle, the walls around the sac may be of a robust nature that may limit the expansion of balloon extensions 122 to a specific diameter based upon the inside diameter of the sac. Furthermore, due to the robust nature of the tissue surrounding the sac, there may be less chance of balloon extensions 122 perforating into the surrounding tissue and, for example, spreading infectious material outside the sac. Hence, balloon extensions 122 may maximally extend 4 or more millimeters from catheter 118, being inhibited from reaching their maximum expansion by the pressure of the walls surrounding the sac.

It should be noted that where extension is manual or automatic, multiple settings are optionally provided for use in various settings.

The length of each balloon extension 122 of the embodiment using two or more balloon extensions 122, may vary in relationship to each other for use in cavities in which asymmetric circumferential and/or axial expansion may be desired. In an embodiment of the invention, in extending balloon extensions 122 inside a pus pocket near nerve tissue such as the sciatic nerve, balloon extensions 122 may extend a millimeter away from catheter 118 on the side that is near the nerve while two or more milliliters away from catheter 118 on the side that is away from the nerve, for example to prevent nerve damage. Optionally, catheter 118 carries markings that allow an operator to determine the orientation of balloon extensions 122 so that the those that extend a shorter distance away from catheter 118 are located near the nerve tissue.

Figure 2C:
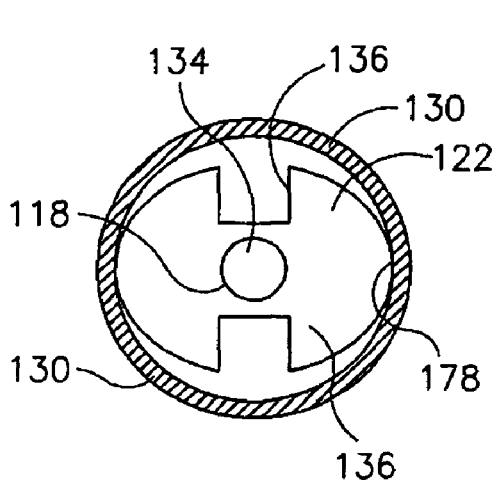
FIG. 2C is a frontal view of a catheter with a conical balloon extension, according to an exemplary embodiment of the present invention.

In an embodiment of the present invention, the one or more balloon extensions have an alternative shape to the balloon extension shown in FIG. 2B. For example, in FIG. 2C, a conical balloon extension 122 has a base 136 near catheter 118 and a bowed section 178 along wall of vein 130. Conical balloon extension 122 may be useful, for example, when the tissue against which it expands requires a more even, robust pressure, for example in a fluid sac located between lung tissue and the rib cage. Multiple balloon extensions 122 in such an application, for example, may cause irritation, and/or perforation of lung tissue.

While for clarity, catheter 118 is shown as being straight, it may be curved, bent, rigid or flexible or otherwise designed for appropriate introduction to any type of body cavity and still be within the scope of this invention. A curved catheter 118 may be useful, for example, in fluid exchange where the surrounding tissue tends to exhibit sharp curves, for example, in alveolar tissue. By incorporating a curved catheter 118 and/or a catheter 118 that is flexible, hence allows curvature to take place, damage to the tissue surrounding an alveolus may be reduced.

Catheter 118 with balloon extensions 122, or other extension embodiments, has application, for example, as a body ingress for insulin derivatives delivered to the body using, for example, an insulin pump. Additionally or alternatively, catheter 118 may be used for lavage of a body organ, wherein sterile fluids are introduced and/or evacuated for the purpose of control of infection. In these latter two applications, catheter 118 is, for example, three or more centimeters in length, based upon the thickness of the body tissue it must traverse in order to reach its targeted fluid exchange area.

In an embodiment of the invention, catheter 118 may have a larger bore, for example 4 millimeters or larger, to accommodate evacuation of exudative material that is highly viscous. Additionally or alternatively, catheter 118 may have a narrower bore, for example one millimeter or less, in order to provide a stream of fluid entering an organ with high pressure that breaks up an infectious nidus so that it can be more efficiently evacuated from the body.

Figure 2D:
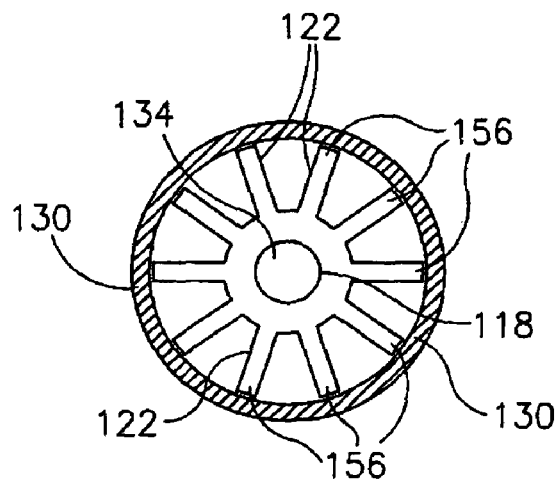
FIG. 2D is a frontal view of a catheter with multiple finger balloon extensions, according to an exemplary embodiment of the present invention.
Figure 2E:
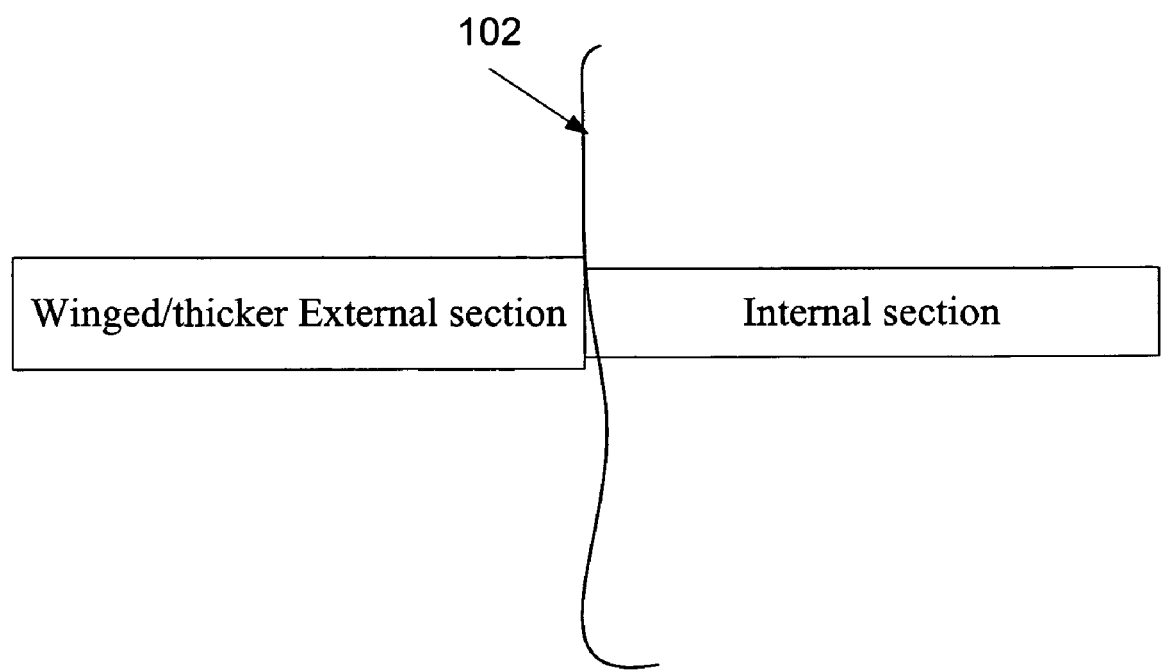
FIG. 2E is a block diagram of an exemplary catheter, for example as depicted in FIGS. 2A-2D, having an internal section in the body of the patient and an external section outside the body of the patient, which is a winged and/or thicker, according to an exemplary embodiment of the present invention.

FIG. 2D illustrates still another design of balloon extension 122 where the one or more extensions are narrow with tips 156 that press a wall of vein 130 when balloon extensions 122 are in an expanded state. This alternative embodiment allows fluid movement within the surrounding cavity even as balloon extensions 122 are expanded. Narrow tips 156 possibly provide an advantage in arterial fluid exchange when catheter 118 is used in an artery were collateral arterial blood flow is missing and/or compromised and occlusion of the artery can cause tissue damage due to lack of blood flow. Narrow tips 156 allow blood flow to proceed even as balloon extensions 122 are extended.

Figure 3:
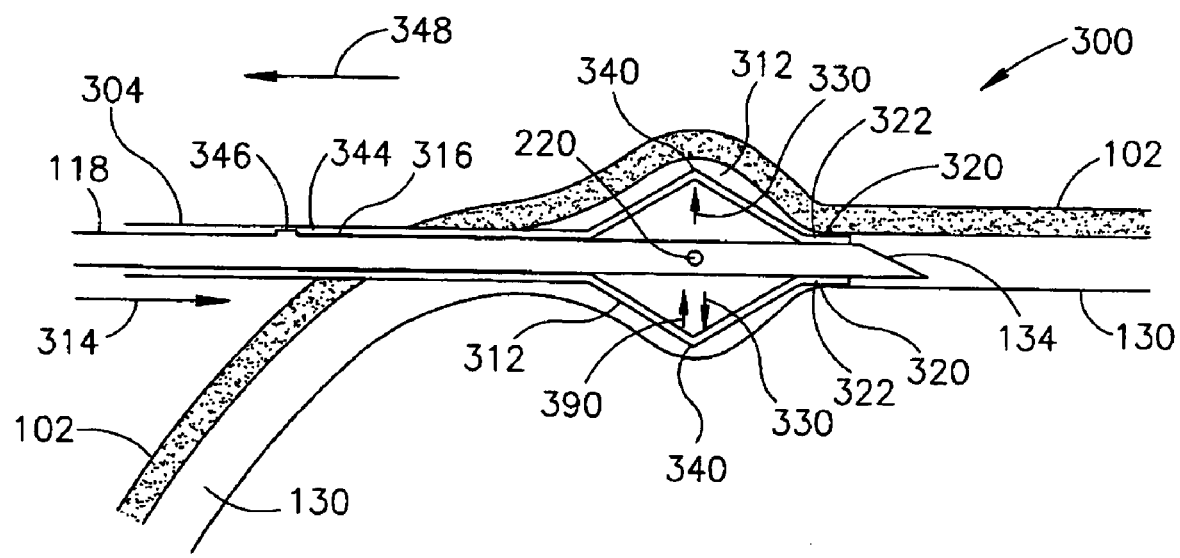
FIG. 3 is a schematic side view of a catheter with multiple deformable extensions, according to an exemplary embodiment of the present invention.

FIG. 3 shows another embodiment of the present invention 300 where the extensions are one or more deformable extensions 312 that push walls of vein 130 away from catheter inlet 134, removing and/or displacing blockages, for example those noted above, allowing fluid intake through catheter 118. Deformable extensions 312 have a deformation area 340 that maintains one position near catheter 118 and a second position, away from catheter 118 which pushes wall of vein 130 away from tip of catheter 134. While two end positions are provided in some embodiments of the invention, for example, using suitable mechanical stops on catheter 118, in other embodiments of the invention multiple (or continuous) intermediate positions are provided, for example by friction between the extension layer and the body of the catheter or by a suitable extension handle. Such mechanisms for providing multiple relative axial positions for two sliding tubes are well known.

Deformable extension 312 has two ends, one end attached to a skin flat 316 and a second end attached to a catheter flat 322. Skin flat 316 projects beyond skin 102 so that it may be easily accessed, for example manually by an operator or by a mechanism, to move in direction 314. Catheter flat 322 is near catheter front inlet 134 and rests against a stop 320 that, for example, is attached to catheter 118. When skin flat 316 moves in direction 314, catheter flat 322 presses against stop 320 and pressure develops in direction 330. This results in deformation area 340 and deformable extension 312 extending away from catheter 118 which pushes walls of vein 130 away from catheter front inlet 134, allowing fluid withdrawal from a body tissue. In some cases, when pressure in direction 314 on skin flat 316 is diminished, the pressure of wall of vein 130 on deformable area 340 in a direction 390 becomes unopposed by pressure in direction 330 and deformable extensions 312 move toward catheter 118.

In an alternative embodiment, deformable extensions 312 comprise an elastic material that naturally maintains a bent position. This embodiment may be helpful in cases where, for example, there is highly resilient tissue surrounding deformable extension 312 and/or force by an operator or a mechanism may be insufficient to easily operate deformable extensions 312.

In this embodiment, a locking tab 344, for example, is incorporated into sheath 304 external to skin 102. Locking tab 344 presses against a notch 346, preventing movement of skin flat 316. When locking tab 344 is moved free of notch 346, as shown in FIG. 3, deformable extension 312 automatically extends in direction 330 due to the action of elastic material at deformable area 340. To return and maintain deformable extension 312 in the non-expanded state, skin flat 316 is moved in direction 348 until locking tab 344 engages notch 346.

While deformation to the side is shown, the deformation may include a forward component as well, for example if the distal "arm" of the extension is considerably shorter than the proximal arm thereof, or if the distal arm is flexible rather than rigid.

Figure 4:
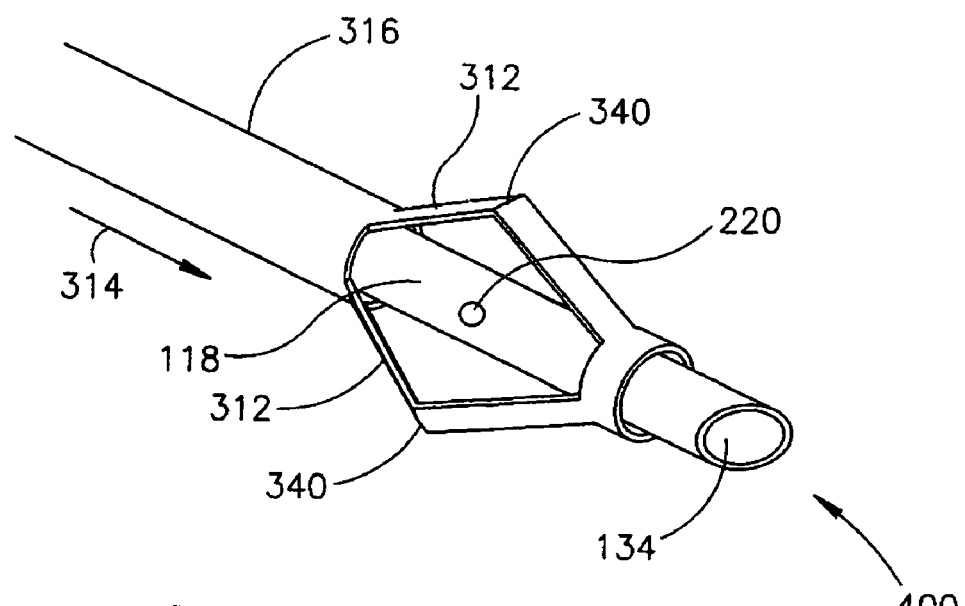
FIG. 4 is an elevational view of a catheter with multiple deformable extensions, according to an exemplary embodiment of the present invention.

FIG. 4 is a side elevation view 400 of catheter 118 demonstrating multiple deformable extensions 312 and side opening 220. The number of deformable extensions 312, for example, may be one, two or even six or eight. In the example shown, the extensions are formed by slotting a tube mounted on the outside of the catheter. Optionally, this tube (e.g., catheter 118) is coated with a thin elastic layer, to reduce the exposure of the blood to sharp angles.

Figure 5:
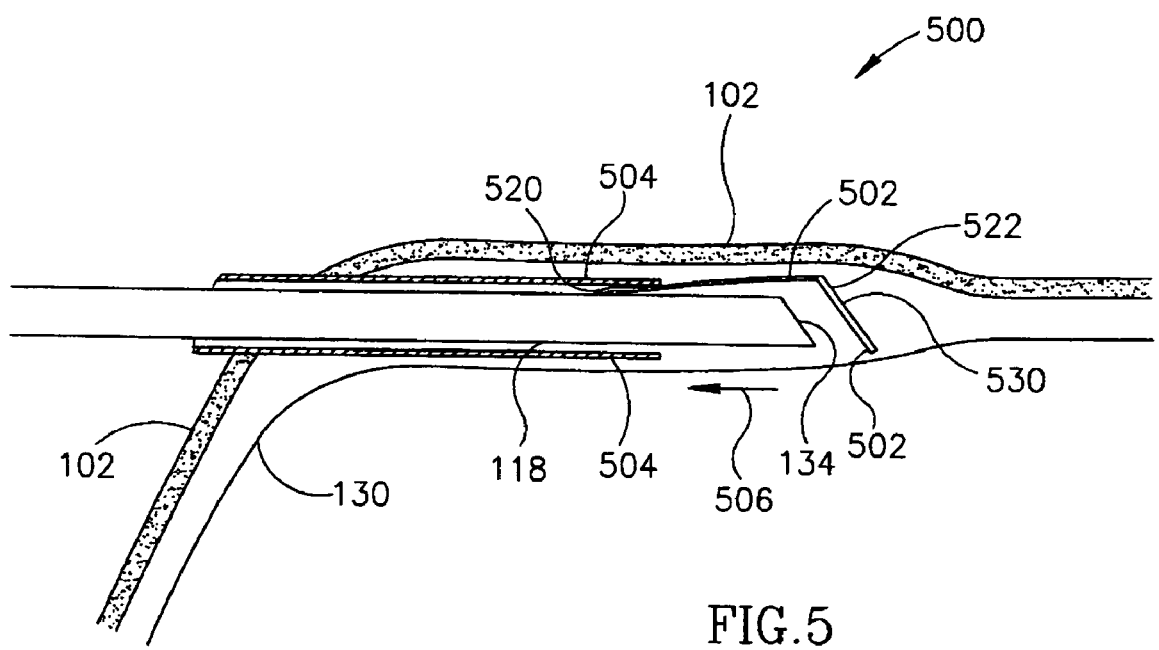
FIG. 5 is a schematic side view of a catheter with resilient extensions, according to an exemplary embodiment of the present invention.

FIG. 5 is a schematic side view 500 of a catheter 118 with resilient extensions 502 which extend away from catheter 118 and exert pressure on walls of vein 130. In an embodiment of the present invention, resilient extensions 502 have two ends, an extension end 522 and an attachment end 520. Attachment end 520 is attached to catheter 118. Further, resilient extensions 502 are contained within a containment sheath 504, near catheter 118. When containment sheath 504 is pulled in a direction 506, resilient extensions 502 are released from containment sheath 504, and extension end 522 extends away from catheter 118, exerting pressure on the walls of vein 130. Such a containment sheath may be used for the embodiment of FIGS. 2-3 as well.

Optionally, one or more resilient extensions 502 have a catheter tip cover 530 that, when resilient extensions 502 are near catheter 118, prevent solids from fluid, such as blood, from building within catheter 118 and causing blockage of fluid exchange. As containment sheath 504 is pulled in direction 506, resilient extensions 502 are released from containment sheath 504, extension end 522 extends away from catheter 118 and catheter tip cover 530 is freed from catheter front inlet 134 to allow exchange of fluid. Optionally, in this and/or other embodiments, after removal is completed, the extensions are retracted and the catheter is sucked out (e.g., by connection to a vacuum source) and/or washed out with a clean solution (e.g., saline solution). The covering of the various openings may be water (blood) tight or be leaky, in various embodiments of the invention.

Optionally, the one or more extensions 502 includes a small section (not shown), for example a short wire, inside catheter 118, so that when the extension is extended, this small portion and any coagulation thereon extend out of the tube. Alternatively or additionally, catheter 118 may be flushed out prior to use.

While radial deflection is shown, this is not required in all embodiments. In an alternative embodiment, the extension is formed as an overtube that also caps inlet 134. Extending the extension, for example by axial or spiral advancing of the overtube, uncaps the inlet. Optionally, the over tube is apertured near its ends. Optionally, these apertures align with one or more apertures formed in catheter 118, when the extensions are activated. In another embodiment of the invention, no actual extension is provided, instead, by rotation of the overtube, an aperture in the overtube aligns with an aperture in catheter 118, to allow flow. Effectively, the portion of the overtube near the aperture serves as an "extension".

Figure 6:
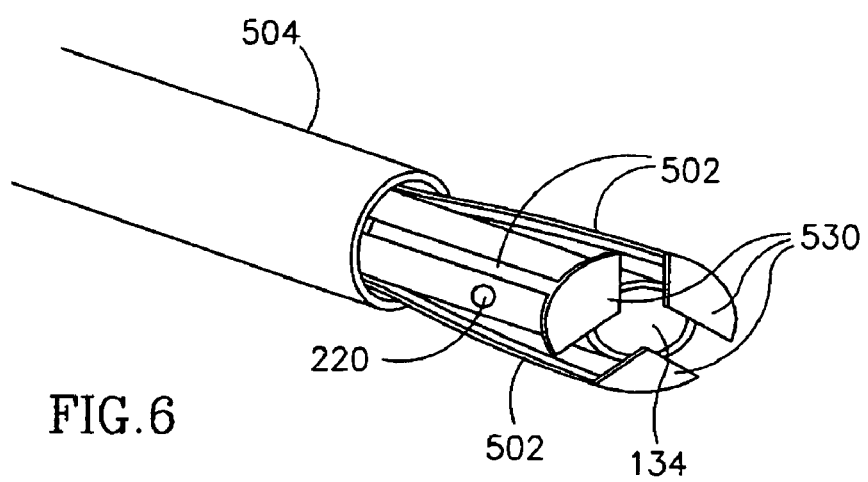
FIG. 6 is a frontal view of a catheter with resilient extensions, according to an exemplary embodiment of the present invention.

FIG. 6 illustrates catheter containment sheath 504 with catheter front inlet 134 surrounded by multiple resilient extensions 502 that are released from containment sheath 504. In an embodiment of the present invention, resilient extensions 502 have catheter tip covers 530 that each partially covers catheter front inlet 134, and together fully cover catheter front inlet 134. This arrangement of multiple, smaller, catheter tip covers 530, optionally allows catheter tip to be freed of catheter tip covers 530 with a smaller movement of resilient extensions 502 than where there is a single, larger, catheter tip cover 530. This allows catheter front inlet 134 to be freed of catheter tip covers 530 when there is resilient tissue, for example, that somewhat resists movement.

While three resilient extensions 502 are shown, as many as six or ten are contemplated by the invention, or as few as one or two resilient extensions 502 are contemplated, for example varying according to the type of tissue, size of tissue cavity, resilience of tissue and/or other tissue qualities, for example noted above. Furthermore, all resilient extensions 502 may have catheter tip covers 530. Additionally or alternatively, some resilient extensions 502, one or none may have catheter tip covers 530.

While an optional opening 220 is shown offset from extensions 502, optionally, extensions 502 selectable uncover opening 220 when the extensions are extended.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. For example, the method of attachment varies, for example, being adhesive based or using other mechanical attachment means such as screws or bolts. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. A venous port adapted to be placed through a body tissue and implanted in a surface vein for the purpose of unimpeded intake of fluid through an aperture thereof, comprising:
   a hollow tube defining at least one aperture configured for the unimpeded intake of fluid when implanted in the surface vein; and
   a plurality of extensions, each operative to be at at least two positions with respect to said at least one aperture, a first position near said at least one aperture and a second position in which at least part of each of said plurality of extensions extends away from said at least one aperture, wherein if said at least one aperture is blocked by an impediment, relative movement of said plurality of extensions with respect to said at least one aperture, from said first position to said second position, operates to dislodge the impediment from said at least one aperture and to open at least one blood passageway among said plurality of extensions;
   wherein said hollow tube has a portion sized and shaped to prevent the insertion of more than 10 cm of said hollow tube in the body of a patient when implanted so that said hollow tube is adapted to be implanted in the surface vein and withstand the unimpeded intake of fluid for a period of one or more days.

2. The venous port according to claim 1 wherein said at least one aperture comprises a front inlet at a front end of said hollow tube.

3. The venous port according to claim 1, wherein said at least one aperture comprises one or more side openings in a side of said hollow tube.

4. The venous port according to claim 1 wherein said at least one aperture comprises at least one front opening at a front end of said hollow tube and at least one side opening in a side of said hollow tube.

5. The venous port according to claim 1 wherein said a plurality of extensions are configured so that moving at least one of said a plurality of extensions from said first position to said second position operates to displace the impediment which comprises an aggregate of solid material.

6. The venous port according to claim 1 wherein said a plurality of extensions are configured so that moving at least one of said a plurality of extensions from said first position to said second position operates to displace the impediment which is down-flow from said hollow tube.

7. The venous port according to claim 1 wherein said a plurality of extensions are configured so that moving at least one of said a plurality of extensions from said first position to said second position operates to displace the impediment which is at least partly within said hollow tube.

8. The venous port according to claim 1 wherein said a plurality of extensions are configured so that moving at least one of said a plurality of extensions from said first position to said second position operates to displace the impediment comprising a venous valve.

9. The venous port according to claim 1 wherein said a plurality of extensions are configured so that moving at least one of said a plurality of extensions from said first position to said second position operates to displace the impediment comprising body tissue.

10. The venous port according to claim 9 wherein the impediment comprises inflamed body tissue.

11. The venous port of claim 1 wherein said hollow tube is adapted to be implanted in the surface vein and withstand the unimpeded intake of fluid for a period of one or more weeks.

12. The venous port of claim 1 wherein said hollow tube is adapted to be implanted in said surface vein and withstand the unimpeded intake of fluid for a period of one or more months.

13. The venous port according to claim 1, comprising an activating mechanism.

14. The venous port according to claim 13 wherein said activating mechanism causes at least one of said a plurality of extensions to extend from said first position to said second position.

15. The venous port according to claim 13 wherein said activating mechanism causes said a plurality of extensions to un-extend from said second position to said first position.

16. The venous port according to claim 13 wherein said activating mechanism is configured for manual activation.

17. The venous port according to claim 13 wherein said activating mechanism is configured for automatic activation.

18. The venous port according to claim 1 adapted so that said relative movement of at least one of said a plurality of extensions occurs prior to an intake of fluid through said at least one aperture.

19. The venous port according to claim 1 adapted so that said relative movement of at least one of said a plurality of extensions occurs during an intake of fluid through said at least one aperture.

20. The venous port according to claim 1 adapted so that said relative movement of at least one of said a plurality of extensions occurs following an intake of fluid through said at least one aperture.

21. The venous port according to claim 1 adapted so that at least some of said relative movement of at least one of said a plurality of extensions takes place irrespective of the unimpeded intake of fluid through said at least one aperture.

22. The venous port according to claim 1 wherein at least part of said plurality of extensions, overlaps a front end of said hollow tube when said at least one extensions are in a first position.

23. The venous port according to claim 1 wherein said at least one aperture is covered by at least one of said a plurality of extensions in said first position.

24. The venous port according to claim 1 wherein said at least one aperture is arranged to be covered when at least one of said a plurality of extensions is in said first position.

25. The venous port according to claim 1 wherein one or more of said hollow tube and said a plurality of extensions comprise a material that prevents or retards aggregation of solids from a bodily fluid.

26. The venous port according to claim 1 wherein one or more of said hollow tube and said a plurality of extensions comprise a material that prevents or retards clot formation.

27. The venous port according to claim 1 wherein one or more of said hollow tube and said a plurality of extensions comprise a material that prevents or retards body tissue inflammatory response.

28. The venous port according to claim 1 wherein one or more of said hollow tube and said a plurality of extensions comprise a material that prevents or retards bacteria colonization.

29. The venous port according to claim 1 wherein at least one of said a plurality of extensions comprises at least one expandable element.

30. The venous port according to claim 29 wherein said at least one expandable element expands when filled with expansion fluid.

31. The venous port according to claim 30, comprising an activating mechanism including a reservoir containing expansion fluid functionally associated with said at least one expandable element.

32. The venous port according to claim 30 wherein said expansion fluid comprises a material that affects the formation of impediments and wherein said at least one expandable element is at least partly permeable to said material.

33. Apparatus according to claim 1 wherein said at least one of said plurality of extensions comprise an extension with a deformable area.

34. Apparatus according to claim 33, wherein when said deformable area deforms, said extension with said deformable area extends from said first position to said second position.

35. Apparatus according to claim 33 wherein when said extension with said deformable area un-extends from said second position to said first position, said deformable area returns to a pre-deformed state.

36. The venous port according to claim 1 wherein said plurality of extensions comprises resilient extensions.

37. Apparatus according to claim 1, comprising a sheath for selectively controlling a said position to which said plurality of extensions extend.

38. Apparatus according to claim 37, wherein in said first position said plurality of extensions are contained within said sheath and in said second position said plurality of extensions exits said sheath to deflect radially.

39. Apparatus according to claim 1, comprising an extension tube of which said plurality of extensions forms a distal section, wherein axial distal motion of said extension tube moves said at least one extension to said second position where said plurality of extensions extends.

40. Apparatus according to claim 39, wherein a distal section of said extension tube is axially fixed to a front of said hollow tube and wherein said extension tube is slotted.

41. The venous port according to claim 1, wherein at least one of said a plurality of extensions is adapted for an arm vein.

42. The venous port according to claim 1, wherein at least one of said a plurality of extensions is adapted for a non-vein vessel.

43. The venous port according to claim 1, wherein said at least two positions are axially displaced.

44. The venous port according to claim 1, wherein said at least two positions are radially displaced.

45. Apparatus according to claim 1, wherein said plurality of extensions do not provide a channel of fluid communication through which a fluid sample can be conducted to outside of the body tissue.

46. The venous port according to claim 1, wherein said hollow tube is comprised of a thicker section outside the body of a patient than inside the body of the patient to prevent entry into the body of the patient.

47. The venous port according to claim 1, wherein said portion of said hollow tube is winged.

48. The venous port according to claim 1, wherein said hollow tube is a port.

49. The venous port according to claim 1, wherein the surface vein is an arm vein.

50. The venous port according to claim 1, wherein the hollow tube has a diameter of 3 millimeters.

51. A method of taking fluid from a vein, the method comprising of:
   implanting an apparatus in a vein, the apparatus comprising of:
      a hollow tube defining at least one aperture; and
      a plurality of extensions, each operative to be at at least two positions with respect to said at least one aperture, a first position near said at least one aperture and a second position in which at least part of each of said plurality of extensions extends away from said at least one aperture, wherein if said at least one aperture is blocked by an impediment, relative movement of said plurality of extensions with respect to said at least one aperture, from said first position to said second position, operates to dislodge the impediment from said at least one aperture and to open at least one blood passageway among said plurality of extensions;
      wherein said hollow tube has a portion sized and shaped to prevent the insertion of more than 10 cm of said hollow tube in the body of a patient when implanted so that said hollow tube is adapted to be implanted in the surface vein and withstand the unimpeded intake of fluid for a period of one or more days;
   taking fluid from the vein through said at least one aperture; and
   dislodging an impediment from said at least one aperture by extending at least one of said plurality of extensions.

* * * * *